(12) United States Patent
Bond et al.

(10) Patent No.: US 6,713,527 B2
(45) Date of Patent: Mar. 30, 2004

(54) ANAESTHETIC BONE CEMENT

(75) Inventors: David M. Bond, Glenburnie (CA); John F. Rudan, Kingston (CA); Michael A. Adams, Kingston (CA)

(73) Assignee: Queen's University at Kingston, Kingston (CA)

(*) Notice: Subject to any disclaimer, the term of this patent is extended or adjusted under 35 U.S.C. 154(b) by 0 days.

(21) Appl. No.: 10/003,769

(22) Filed: Nov. 15, 2001

(65) Prior Publication Data

US 2002/0137813 A1 Sep. 26, 2002

Related U.S. Application Data

(63) Continuation of application No. 09/365,175, filed on Aug. 2, 1999, which is a continuation-in-part of application No. 08/799,007, filed on Feb. 7, 1997, now abandoned, and a continuation-in-part of application No. 08/825,943, filed on Apr. 1, 1997, now Pat. No. 6,355,705.

(30) Foreign Application Priority Data

Feb. 2, 1998 (WO) .............. PCT/CA98/00060

(51) Int. Cl.⁷ .............................. A61L 24/06
(52) U.S. Cl. .............. 523/118; 523/105; 523/113; 523/122; 424/422; 424/423; 424/487; 514/816; 514/817; 514/818; 623/16
(58) Field of Search ........................ 523/113, 118, 523/105, 122; 424/422, 423, 487; 514/816, 817, 818; 623/16

(56) References Cited

U.S. PATENT DOCUMENTS

| | | | | |
|---|---|---|---|---|
| 4,005,191 A | * | 1/1977 | Clark | 424/687 |
| 4,341,691 A | | 7/1982 | Anuta | 523/116 |
| 4,588,583 A | * | 5/1986 | Pietsch et al. | 514/772.4 |
| 4,718,910 A | * | 1/1988 | Draenert | 433/202.1 |
| 4,722,948 A | * | 2/1988 | Sanderson | 523/113 |
| 4,765,983 A | | 8/1988 | Takayanagi et al. | 424/434 |
| 4,791,150 A | | 12/1988 | Braden et al. | 523/117 |
| 4,837,279 A | | 6/1989 | Arroyo | 525/193 |
| 4,843,112 A | | 6/1989 | Gerhart | 523/114 |
| 4,868,237 A | | 9/1989 | Hoff et al. | 524/407 |
| 4,900,546 A | * | 2/1990 | Posey-Dowty et al. | 514/29 |
| 4,910,259 A | | 3/1990 | Kindt-Larsen et al. | 525/259 |
| 4,978,391 A | | 12/1990 | Jones | 106/35 |

(List continued on next page.)

FOREIGN PATENT DOCUMENTS

| | | |
|---|---|---|
| AU | 55167/86 | 1/1986 |
| EP | 0164483 A1 | 12/1984 |
| EP | 164483 * | 12/1985 |
| EP | 0301759 A2 | 7/1988 |
| EP | 301759 A * | 2/1989 |
| JP | 53-015409 | 5/1978 |
| JP | 1-143829 | 6/1989 |
| JP | 01151952 | 6/1989 |
| WO | WO 88/05650 | 1/1988 |
| WO | WO-88 05650 A * | 8/1988 |

OTHER PUBLICATIONS

"Standard Specification for Acrylic Bone Cement", Designation F451–95, ASTM Subcommittee F04.11, 1995.

"Total Hip Joint Replacement", NIH Consens Statement Online Mar. 1–3, 1982 4(4):1–11.

Alexander et al., "Comparison of ondansetron, metoclopramide and placebo as premedicants to reduce nausea and vomiting after major surgery", Abstract, *Anasthesia,* vol. 52(7):695–700, (1997).

(List continued on next page.)

*Primary Examiner*—Margaret Medley
(74) *Attorney, Agent, or Firm*—Lahive & Cockfield, LLP

(57) ABSTRACT

The invention relates to surgical bone cement compositions and more particularly to bone cement compositions having aneasthetic properties, and to methods for producing analgesia.

15 Claims, 6 Drawing Sheets

U.S. PATENT DOCUMENTS

| | | | |
|---|---|---|---|
| 5,069,905 A | 12/1991 | Lidor et al. | 424/423 |
| 5,085,861 A | 2/1992 | Gerhart et al. | 424/78.17 |
| 5,100,241 A | 3/1992 | Chan | 366/139 |
| 5,106,614 A * | 4/1992 | Posey-Dowty et al. | 424/423 |
| 5,110,720 A * | 5/1992 | Csanyi et al. | 433/215 |
| 5,258,420 A * | 11/1993 | Posey-Dowty et al. | 424/78.18 |
| 5,276,070 A | 1/1994 | Arroyo | 523/117 |
| 5,277,739 A | 1/1994 | MZüller et al. | 156/330.9 |
| 5,324,519 A | 6/1994 | Dunn et al. | 424/426 |
| 5,334,626 A | 8/1994 | Lin | 523/116 |
| 5,366,756 A | 11/1994 | Chesterfield et al. | 427/2.26 |
| 5,374,427 A | 12/1994 | Stille et al. | 424/425 |
| 5,443,182 A | 8/1995 | Tanaka et al. | 222/137 |
| 5,512,610 A | 4/1996 | Lin | 523/116 |
| 5,660,854 A * | 8/1997 | Haynes et al. | 424/442 |
| 5,681,873 A | 10/1997 | Norton | 523/115 |
| 5,847,046 A | 12/1998 | Jiang | 524/42 |
| 5,888,533 A * | 3/1999 | Dunn | 424/423 |
| 5,919,473 A | 7/1999 | Elkhoury | 424/422 |
| 6,020,396 A | 2/2000 | Jacobs | 523/116 |
| 6,080,801 A | 6/2000 | Draenert et al. | 523/115 |
| 6,160,033 A | 12/2000 | Nies | 523/116 |
| 6,166,173 A | 12/2000 | Mao | 528/398 |
| 6,273,916 B1 * | 8/2001 | Murphy | 623/23.62 |
| 6,355,705 B1 * | 3/2002 | Bond et al. | 523/118 |

OTHER PUBLICATIONS

Arac et al., "Prevention of aprotonin of the hypotension due to acrylic cement implantation into the bone", Abstract, *Curr. Ther. Res., Clin. Expo.,* vol. 28/4:554–557, (1980).

Bachmann et al., "Intrathecal infusion of bupivacaine with or without morphine for postoperative analgesia after hip and knee arthroplasty", Abstract, *Br. J. Anaesth.,* 78:666–670, (1997).

Badner, N.H. et al., "Intra–articular injection of bupivacaine in knee–replacement operations," *J. Bone and Joint Surg.* 78–A:734–738 (1996).

Baker, A.S. et al., "Release of Gentamicin from Acrylic Bone Cement", *J. Bone and Joint Surg.* 70–A:1551–1557 (1988).

Bayston, R., R.D.G. Milner, "The Sustained Release of Antimicrobial Drugs from Bone Cement, an Appraisal of Laboratory Investigations and Their Significance," *J. Bone and Joint Surg.* 64–B:460–464, (1982).

Brien, W. et al., "Antibiotic Impregnated Bone Cementin Total Hip Arthroplasty, an In Vivo Comparison of the Elution Properties of Tobramycin and Vancomucin," *Clinical Orth. and Related Research* 296:242–248, (1993).

Buchholz, H.W. et al., "Antibiotic–loaded acrylic cement: Current concepts", *Clinical Orthopaedics and Related Research,* 190:96–108 (1984).

Duncan, C. et al., "The Role of Antibiotic–Loaded Cement in the Treatment of an Infection After a Hip Replacement," *J. of Bone and Joint Surg.* 76–A:1742–1751, (1994).

Elson, R.A. et al., "Antibiotic–loaded acrylic cement", *Journal of Bone and Joint Surgery,* 59–B:200–205 (1977).

Enneking et al., "Cardiac arrest during total knee replacement using a long–term prothesis", Abstract, *J. Clinical Anesthesia,* vol. 7/3:253–263, (1995).

Gruntova, Z. et al., "Bioadhesive Preparations with Local Anesthetic Agents for Dental Use", Abstract, *Chemical Abstracts,* vol. 108, No. 16, Abstract No. 137849, Apr. 18, 1988.

Hadgraft, J. "Calculations of drug release rates from controlled release devices. The slab", *Interntl. J. Pharma.* 2:177–194 (1979).

Hughes, S. et al., "Cephalosporins in Bone Cement, Studies in Vitro and In Vivo," *J. Bone and Joint Surg.* 61–B:98–100, (1979).

Law, H.T. et al., "In vitro measurement and computer modelling of the diffusion of antibiotic in bone cement", *J. Biomed Eng.* 8:1490155 (1986).

Marks, K.E. et al., "Antibiotic–impregnated acrylic bone cement", *Journal of Bone and Joint Surgery* 58–A:358–364 (1976).

Murray, W.R., "Use of antibiotic–containing bone cement", *Clinical Orthopaedics and Related Research* 190:89–95 (1984).

Puronto, M., "Hyperbares Bupiacain 1% (Marcain®/Carbostesin®/ schwer) bei orthopädischen Hemispinalanaesthesien", *Anaesthesist,* vol. 24:408–411 (1975).

Ravin, C.E. et al., "In vitro effects of lidocaine on anaerobic respiratory pathogens and strains of *Hemophilus influenzae*", *Chest* 72:439–441 (1975).

Rosenburg, P.H. et al., "Antimicrobial activity of bupivacaine and morphine", *Anesthesiology* 62:178–179 (1985).

Tryba, M. et al., "Histaminfreisetzung und kardiovaskuläre Reaktionen nach Implantation von Knochenzement bei totalem Hüftgelenkersatz (Histamine release and cardiovascular reactions to bone cement used in total hip replacement", *Anaesthesist,* vol. 40:25–32 (1991), (See also Abstract in English).

Wasserlauf, S. et al., "The release of cytotoxic drugs from acrylic bone cement", *Hospital for Joint Diseases* 53:68–74 (1993).

Watts, N.H. et al., "The mechanical properties of antibiotic–loaded acrylic cement", Abstract, Final Program of the Second Annual Meeting of the Society of Biomaterials, p. 69 (1976).

Yamashita et al., "Effect of bupivacine on muscle tissues and new bone formation induced by demineralized bone matrix gelatin," Abstract, *Acta. Anat.,* vol. 141(1)1–7 (1991).

Zawadzki, A. et al. "Assessment of Methods of Anaesthesia used for Total Alloplasty of Hip Joint with Application of Bone Cement", *Anaesth. Resus. Inten. Therap.,* vol. 4(3):181–185 (1976).

* cited by examiner

ANAESTHETIC BONE CEMENT

CROSS-REFERENCE TO RELATED APPLICATIONS

This application is a continuation application of application Ser. No. 09/365,175 filed on Aug. 2, 1999, now abandoned which in turn is a continuation-in-part application of Ser. No. 08/799,007 filed on Feb. 7, 1997, (abandoned) and Ser. No. 08/825,943 filed on Apr. 1, 1997 now U.S. Pat. No. 6,355,705. This application also claims priority to International Application No. PCT/CA98/00060 filed on Feb. 2, 1998. The contents of all of the aforementioned application (s) are hereby incorporated by reference.

FIELD OF THE INVENTION

This invention relates to surgical bone cement compositions and more particularly to bone cement compositions having anaesthetic properties, and to methods for producing analgesia.

BACKGROUND OF THE INVENTION

Polymer based surgical bone cements have been used for many years to fill voids in bones and to improve fixation of implanted orthopaedic prosthetic devices. Typically such cements contain polymers or copolymers of alkyl methacrylate and/or copolymers of methyl methacrylate with methyl acrylate or styrene. The liquid compound consisting of esters of acrylic or methacrylic acid (typically methyl methacrylate) is packaged in an ampoule, possibly with additives such as premature polymerization preventers such as hydroquinone, and curing promoters such as N,N-dimethyl-p-toluidine. A polymerization initiator, typically an organic peroxy compound such as powdered benzoyl peroxide, is combined with the polymeric component and a radiopacifier (such as barium sulphate or zirconium dioxide) for rendering the bone cement opaque to X-rays. The polymeric materials are generally sterilized by either irradiation or gas sterilization. In use, typically a bone is cut and prepared to receive a surgical implant and then the liquid and dry components of the cement, contained in the ampoule and powder bag are mixed together to form a paste which can then be applied by the surgeon to the cut bone. The implant can then be set in the paste which, when fully polymerized, forms a continuous solid interface between the implant and the bone.

It is also known to incorporate therapeutic or diagnostic substances into the bone cement for various purposes. For example, U.S. Pat. No. 4,900,546, issued Feb. 13, 1990, to Posayn Dowty et al., teaches the incorporation of antibiotics such as gentamycin, penicillin and tetracycline; anti-cancer drugs; anti-inflammatory drugs; immuno-stimulants; immuno-suppressants; osteogenic promoters and diagnostic substances such as radioactive tracers. While some anti-inflammatory drugs may have analgesic properties, such compounds are not anaesthetics.

Although local anaesthetics, such as lidocaine and prilocaine are known to have potent anti-microbial activity (anti-bacterial and anti-fungal), when used in relatively high dosages (0.5–2% solution) (*J. Infect. Diseases*, 121:597–607, 1970), heretofore such anaesthetic compounds have not been incorporated into bone cements for the promotion of anaesthesia. It has now been found that substantial pain relief can be achieved by incorporating into a known bone cement composition a local anaesthetic at a dosage level several orders of magnitude lower than would be required to achieve an anti-microbial effect with such anaesthetic.

OBJECT OF THE INVENTION

An object of the present invention is to provide novel bone cement compositions which incorporate an anaesthetic, and have analgesic properties. Another object of this invention is to provide a method for producing analgesia in the vicinity of a bone surgery site.

SUMMARY OF THE INVENTION

By a broad aspect of this invention, there is provided an anaesthetic bone cement comprising a bone cement composition including an effective amount up to about 5% by weight of an anaesthetic, preferably a local anaesthetic.

By a preferred aspect of this invention, there is provided an anaesthetic bone cement composition comprising: (a) a liquid monomeric (meth)acrylate composition; (b) a powder comprising at least one of a homopolymer and a copolymer of methyl methacrylate containing an effective amount of a polymerization initiator and a radiopacifier; and (c) an effective amount up to about 5% by weight of said bone cement composition of a local anaesthetic.

An anaesthetic bone cement composition in accordance with the invention includes a local anaesthetic in a physical form such as, for example, liquids and solids, and a chemical form such as, for example, acids and bases. A local anaesthetic is released from the bone cement in a preselected characteristic release profile that is determined by at least one of chemical form and physical form of the anaesthetic. An anaesthetic bone cement composition according to the invention comprises an anaesthetic in an amount between about 0.007% and about 5% by weight of said cement composition. An anaesthetic bone cement composition according to the invention can comprise a local anaesthetic provided in at least two different forms, the forms being, for example, acids, bases, solids, and liquids. Also in accordance with the invention, an anaesthetic bone cement composition can comprises a combination of at least two anaesthetics selected from the group consisting of lidocaine, bupivacaine, prilocaine and tetracaine. When a combination of two or more different anaesthetics are included in the bone cement composition of the invention, they can be in two different forms, the forms being selected from the group consisting of acids, bases, solids, and liquids, or they can be of the same form.

By another aspect of this invention, there is provided a process for producing an anaesthetic bone cement comprising combining: (a) a liquid monomeric (meth)acrylate; (b) a powdered component comprising at least one of a homopolymer and a copolymer of methyl methacrylate, an effective amount of a polymerization initiator and a radiopacifier; and (c) an effective amount up to about 5% by weight of a local anaesthetic.

By yet another aspect of this invention there is provided a method for producing analgesia at an orthopaedic implant site in a patient, comprising cutting and preparing a bone at said site to receive said implant and applying to said prepared bone a bone cement composition comprising: (a) a liquid monomeric (meth)acrylate composition; (b) a powder comprising at least one of a homopolymer and a copolymer of methyl methacrylate containing an effective amount of a polymerization initiator and a radiopacifier; and (c) an effective amount up to about 5% by weight of said bone cement composition of a local anaesthetic.

According to the method of the invention, a local anaesthetic included in a bone cement composition can be in a physical form such as, for example, liquids and solids, and a chemical form such as, for example, acids and bases. A local anaesthetic is released from the bone cement in a preselected characteristic release profile that is determined by at least one of chemical form and physical form of the anaesthetic. An anaesthetic bone cement composition according to the method of the invention comprises an anaesthetic in an amount between about 0.007% and about 5% by weight of said cement composition. An anaesthetic bone cement composition according to the method of the invention can comprise a local anaesthetic provided in at least two different forms, the forms being, for example, acids, bases, solids, and liquids. Also in accordance with the method of the invention, an anaesthetic bone cement composition can comprises a combination of at least two anaesthetics selected from the group consisting of lidocaine, bupivacaine, prilocaine and tetracaine. When the method of the invention involves use of a combination of two or more different anaesthetics, they can be in two different forms, the forms being selected from the group consisting of acids, bases, solids, and liquids, or they can be of the same form.

DETAILED DESCRIPTION OF THE INVENTION

Figure 1:
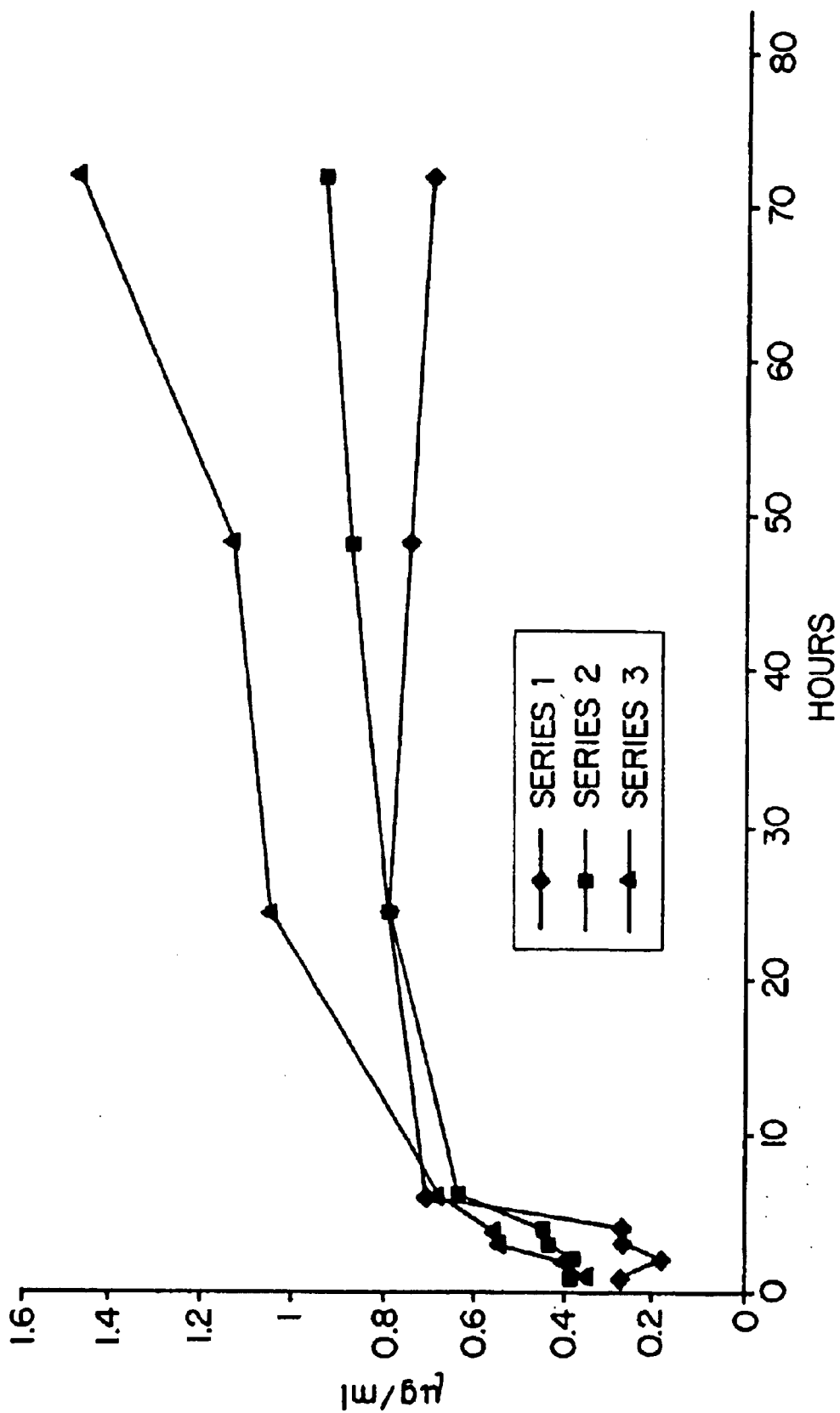
FIG. 1 is a graph showing release of lidocaine from Howmedica bone cement.

By one aspect, this invention pertains to compositions comprising bone cement and an anaesthetic, preferably a local anaesthetic. The compositions of the invention provide a means by which the anaesthetic can be delivered precisely to the site where it is required, for reduction or elimination of pain, simultaneously with the application of bone cement. Compositions of the invention are useful in, but not limited to, surgical procedures involving, for example, manipulation, repair, and replacement of bone and of joints between bones. A typical example of a procedure in which compositions of the invention may be employed is hip replacement surgery. Compositions according to the invention are therefore also useful in procedures in which prosthetic devices or orthopaedic implants are attached to bone. In general, therefore, the compositions of the invention may be employed in any surgical procedure in which bone cement is employed and analgesia is desired.

One advantage of the compositions according to the invention is that the combination of bone cement and an anaesthetic does not result in any reduction in efficacy of the anaesthetic or of the bone cement. Moreover, the combination of bone cement and anaesthetic according to the invention provides a sustained release of the anaesthetic over a prolonged period such as, for example, several days, eliminating the need for repeated administration of anaesthetic. A further advantage of the compositions of the invention is that delivery of the anaesthetic precisely to the source of pain permits smaller doses of anaesthetic to be used, relative to conventional modes of administration such as intramuscular injection. Further, local delivery of the anaesthetic to the site where it is required may provide enhanced efficacy.

Bone cements suitable for use in the compositions of the invention include any commercially available bone cements generally comprising a liquid monomeric (meth)acrylate composition and a powder comprising at least one of a homopolymer and a copolymer of methyl methacrylate containing an effective amount of a polymerization initiator and a radiopacifier. Suitable bone cements are, for example, Howmedica Simplex® (Limerick, Ireland), Zimmer Osteobond™ (Warsaw, Ind.), and DePuy® GMW3™ and CMW Endurance™ (Warsaw, Ind.). DePuy CMW3 is a preferred bone cement. However, the invention is not limited to these bone cements and others may be equally suitable.

Anaesthetics suitable for use in the compositions of the invention are, for example, lidocaine, bupivacaine, prilocaine (amide family), and tetracaine (ester family). However, the invention is not limited to these anaesthetics and others may be equally suitable. A preferred anaesthetic is Xylocaine® (Astra Pharmaceuticals, Sodertalje, Sweden) brand of lidocaine. The compositions of the invention contain an effective amount of the anaesthetic, which amount is up to about 5% by weight of the bone cement composition. In some cases, the anaesthetic incorporated in the bone cement composition may be provided in a precursor (or "prodrug") form which is converted in vivo to an anaesthetic that produces analgesia according to the invention. (See R. B. Silverman, *The Organic Chemistry of Drug Design and Drug Action*, Academic Press, Chapter 8, 1992.) Prodrugs (for example, an ester which is hydrolyzed in vivo) are employed in the art to alter biodistribution of an active compound or to modify metabolic or kinetic properties thereof.

As used herein, the term "effective amount" means an amount of anaesthetic required to achieve the desired result of reduction or elimination of pain.

As used herein, the term "anaesthetic" refers to a compound that reversibly depresses neuronal function, producing loss of ability to perceive pain or other sensations.

As used herein, the term "local anaesthetic" refers to a compound that reversibly depresses neuronal function, producing loss of ability to perceive pain or other sensations, the local anaesthetic acting locally, i.e., at the site or vicinity of its application, to prevent perception of pain.

Anaesthetics are generally amides or ester compounds which depress neuronal function and thus deaden or block pain by inhibiting the neural transmission of pain signals. Anaesthetics are therefore different from NSAID analgesic compounds such as aspirin or acetaminophen which act in an entirely different manner to provide analgesia but not anaesthesia.

As used herein, the term "analgesia" refers to a neurological or pharmacological state characterized by an absence of normal sensibility to pain, without an effect on consciousness. Accordingly, painful stimuli are either not perceived at all, or they are moderated such that, even though they may still be perceived, they are no longer painful.

The present invention is concerned with the use of local anaesthetics, such as lidocaine, bupivacaine, prilocaine (amide family), and tetracaine (ester family) to provide analgesia in body tissues surrounding a surgical site in which a bone cement has been employed.

By another aspect, this invention pertains to a process for producing an anaesthetic bone cement composition comprising combining a commercially available bone cement such as, but not limited to, Howmedica Simplex, Zimmer Osteobond, and DePuy CMW3 and CMW Endurance, with an effective amount up to about 5% by weight of a local anaesthetic. Bone cements suitable for use in the process of the invention generally comprise a liquid monomeric (meth) acrylate composition and a powder comprising at least one of a homopolymer and a copolymer of methyl methacrylate containing an effective amount of a polymerization initiator and a radiopacifier. Examples of anaesthetics suitable for use in the process of the invention are lidocaine, bupivacaine, prilocaine (amide family), and tetracaine (ester family), and others may be equally suitable.

By yet another aspect, this invention pertains to a method for producing analgesia in a patient at the site of a surgical procedure involving manipulating, repairing, and/or replacing bone and joints between bones, and including, for example, implanting prosthetic or orthopaedic devices. The method of the invention comprises preparing bones at the site and applying to the prepared bones a bone cement composition comprising a liquid monomeric (meth)acrylate composition, a powder comprising at least one of a homopolymer and a copolymer of methyl methacrylate containing an effective amount of a polymerization initiator and a radiopacifier; and an effective amount up to about 5% by weight of the bone cement composition of an anaesthetic. Bone cements suitable for use in the method of the invention include, but are not limited to, commercially available bone cements such as Howmedica Simplex, Zimmer Osteobond, and DePuy CMW3 and CMW Endurance. Anaesthetics suitable for use in the method of the invention include lidocaine, bupivacaine, prilocaine (amide family), and tetracaine (ester family), and others may be equally suitable.

Figure 2:
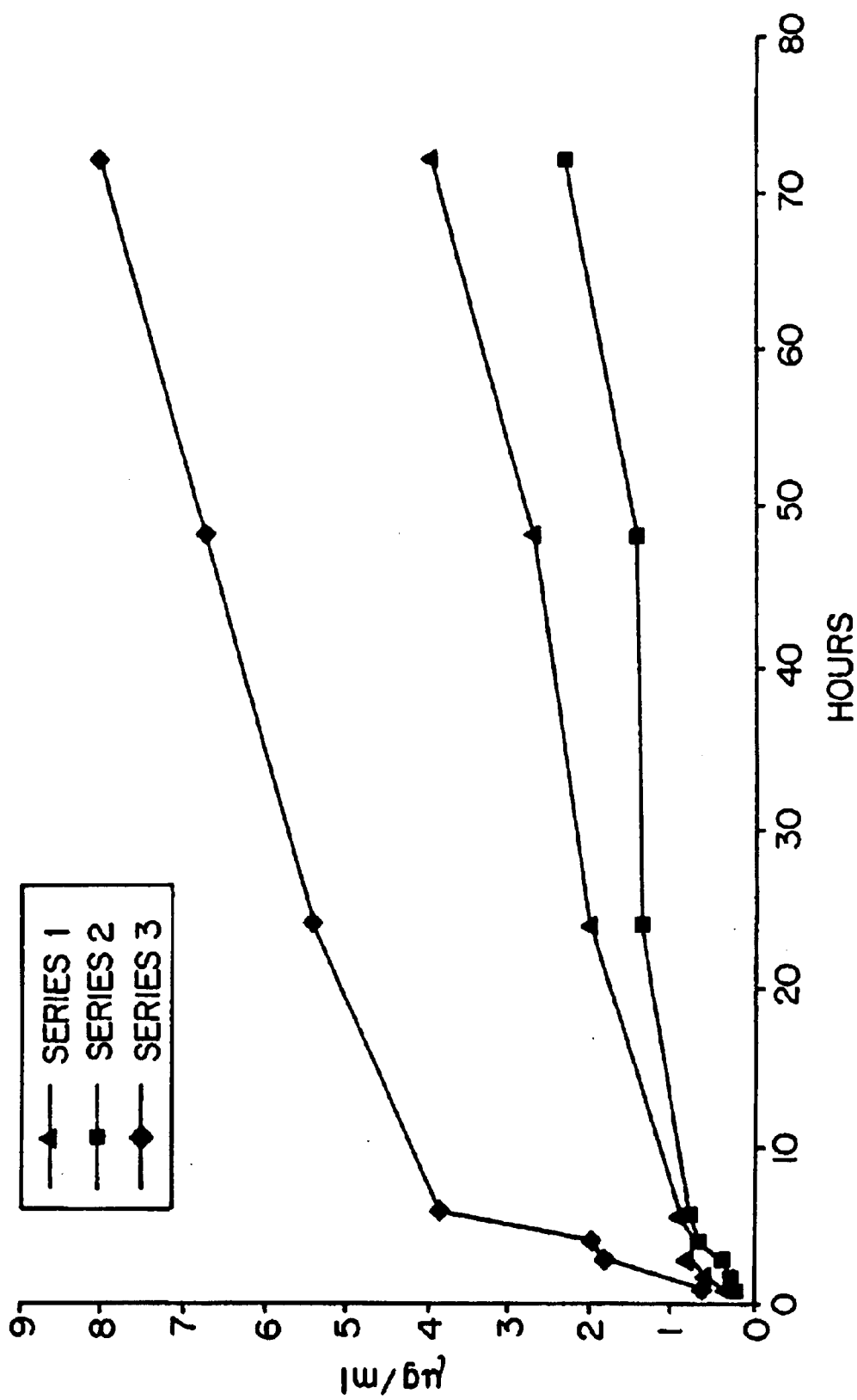
FIG. 2 is a graph showing release of lidocaine from Zimmer bone cement.
Figure 3:
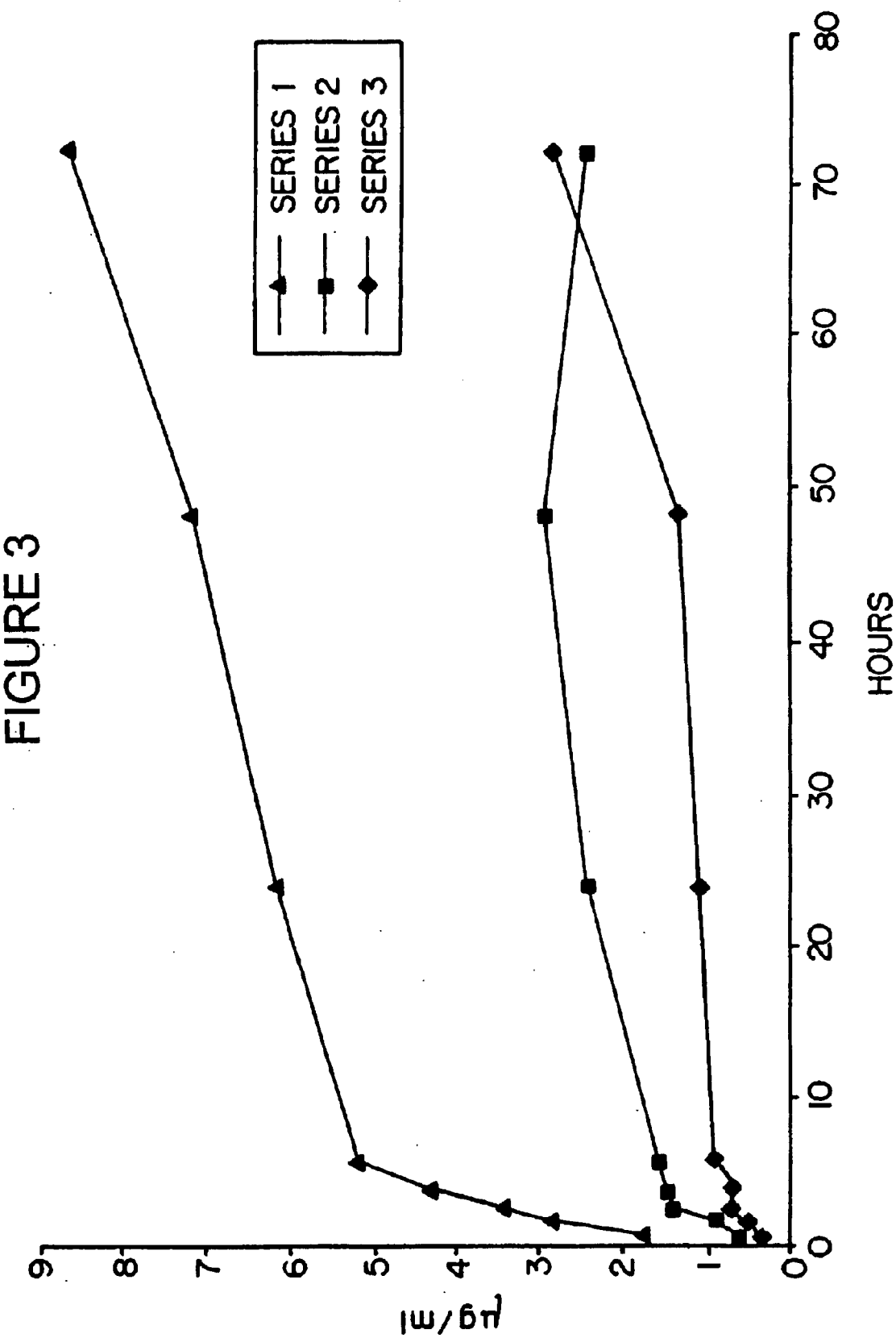
FIG. 3 is a graph showing release of lidocaine from DePuy CMW3 bone cement.

To determine whether local anaesthetics elute from a bone cement containing from about 2.0% to about 5.0% by weight of the anaesthetic, a series of elution studies were performed in which lidocaine (Xylocaine, Astra Pharmaceuticals) was combined with Howmedica, Zimmer, and DePuy bone cement (see Example 1). The elution profiles shown in FIGS. 1, 2, and 3 indicate that this form of lidocaine is released from the bone cement mixture in an amount proportional to the amount of lidocaine in the mixture. The elution profiles further indicate that adequate amounts of lidocaine are released from bone cement to provide the desired efficacy and hence that concentrations of the anaesthetic less than 2% by weight of the bone cement also would provide the desired efficacy.

Anaesthetics suitable for use according to the invention are available as liquids and solids, wherein the solid form is a crystalline powder. In addition, anaesthetics such as lidocaine are also available in base or acid (HCl) forms. Lidocaine used in the studies of Example 1 was crystalline lidocaine base, whereas the studies described in Example 2 concern the release characteristics of alternate forms of anaesthetics when combined with bone cement.

The studies of Example 2 employed crystalline lidocaine base from three manufacturers (Sigma, St. Louis, Mo.; Spectrum, Gardena, Calif.; and Wyckoff, South Haven, Mich.) and Depuy CMW3 and CMW Endurance bone cement. Studies examined the effects of manufacturer of anaesthetic, type of anaesthetic (i.e., lidocaine vs. prilocaine), physical form (i.e., crystalline vs. liquid), particle size of crystalline anaesthetic, type of bone cement (CMW3 vs. CMW Endurance), concentration of anaesthetic (about 0.008% to about 3.5% by weight of bone cement), and chemical form (base vs. HCl), on release profiles (i.e., the amount of anaesthetic released after a given period and the change in rate of elution of anaesthetic over time).

The studies of Example 2 demonstrate that lidocaine currently available from three different manufacturers has the same release characteristics when combined with bone cement according to the invention. In addition, although crystalline forms of anaesthetic from different manufacturers may vary with respect to the proportions of different-sized particles present, particle size does not affect the overall release of anaesthetic after a period of 72 hours. However, as smaller particles of anaesthetic elute faster than larger particles, particularly in the case of lidocaine HCl, particle size should be considered in preparing compositions of the invention when specific elution profiles are desired. For example, by incorporating primarily smaller particles (e.g., 75 to 150 um, see Example 2), a bone cement composition having faster initial release of anaesthetic, and a relatively shorter overall period of release, can be prepared. Conversely, by incorporating primarily larger particles (e.g., >250 um), a bone cement composition having slower initial release of anaesthetic, and a relatively longer overall period of release, can be prepared. Thus it can be seen how anaesthetic bone cement compositions according to the invention may be prepared in various ways to suit specific applications.

The Example 2 studies demonstrate yet another way in which anaesthetic bone cement compositions according to the invention may be prepared to suit specific applications. Specifically, the type of bone cement employed can be used to control the characteristics of the release of anaesthetic. For example, the studies show that, when employing DePuy CMW3, crystalline lidocaine base, crystalline lidocaine HCl, and liquid prilocaine base, are eluted in greater quantities both initially and after 72 hours, than when employing Depuy CMW Endurance bone cement. Therefore, as discussed above with respect to the effect of particle size on anaesthetic release profiles, the use of a specific brand of bone cement in combination with a specific anaesthetic can provide an anaesthetic bone cement with a desired release profile. The profile can be optimized, for example, for fast or slow initial release, as required for a specific therapeutic application. Suitable combinations of bone cement and anaesthetic would be determined through routine experimentation using techniques described in the below examples. Although studies involving bone cement from other manufacturers are not described in Example 2, it is expected that other combinations of bone cement and forms of anaesthetic would similarly provide different release profiles suitable for a range of applications.

Figure 5A:
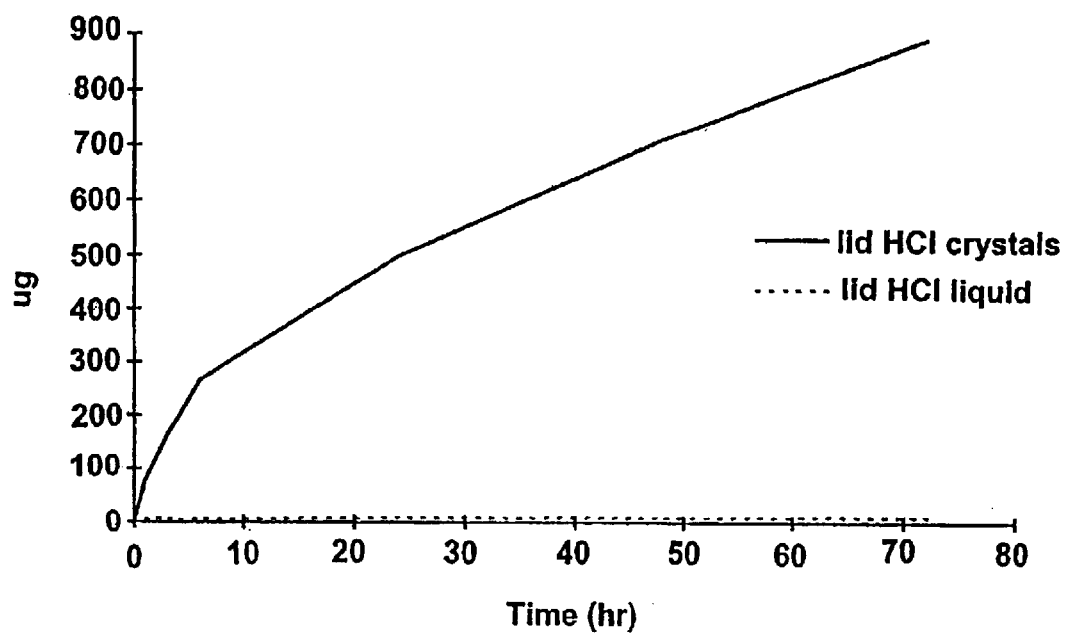
FIGS. 5A and 5B is a graph showing release profiles of crystalline and liquid lidocaine HCl from DePuy CMW3 bone cement.
Figure 5B:
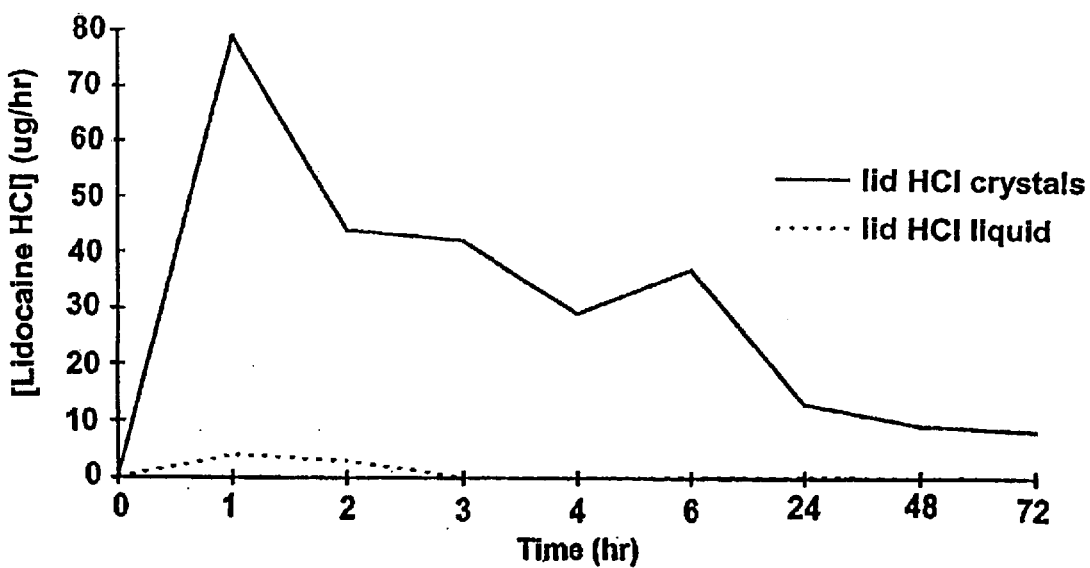

The studies of Example 2 further indicate that the choice of acid or base form of an anaesthetic can substantially affect how much of the anaesthetic is released from the bone cement. For example, when crystalline lidocaine is combined with DePuy CMW3 bone cement, there is substantially more total release of the anaesthetic after 72 hours if lidocaine HCl is used. Similarly, the physical form of anaesthetic is a variable that significantly affects the release of anaesthetic when combined with, for example, DePuy CMW3 bone cement. For example, as shown in FIG. 5, there is substantial release of crystalline lidocaine HCl, and only a small release of liquid lidocaine HCl. It is apparent from these studies that the opposite applies for prilocaine base, wherein release of the liquid form was superior to that of the crystalline form. It is again evident that a desired release profile of an anaesthetic bone cement according to the invention can be designed by selecting, for example, a base or HCl, or a liquid or crystalline, form of an anaesthetic in combination with a suitable bone cement. The invention also contemplates the incorporation of a combination of anaesthetics with different properties into bone cement. Such a combination would comprise, for example, two or more different anaesthetics (e.g., lidocaine and prilocaine), or two or more different forms of an anaesthetic (e.g. HCl and base, or crystalline and liquid). Provision of such a combination of anaesthetics into bone cement would allow the release profile of anaesthetics, and hence profile of the analgesia produced thereby, to be further customized for particular therapeutic applications. All such combinations are considered to be within the scope of the present invention.

Figure 6A:
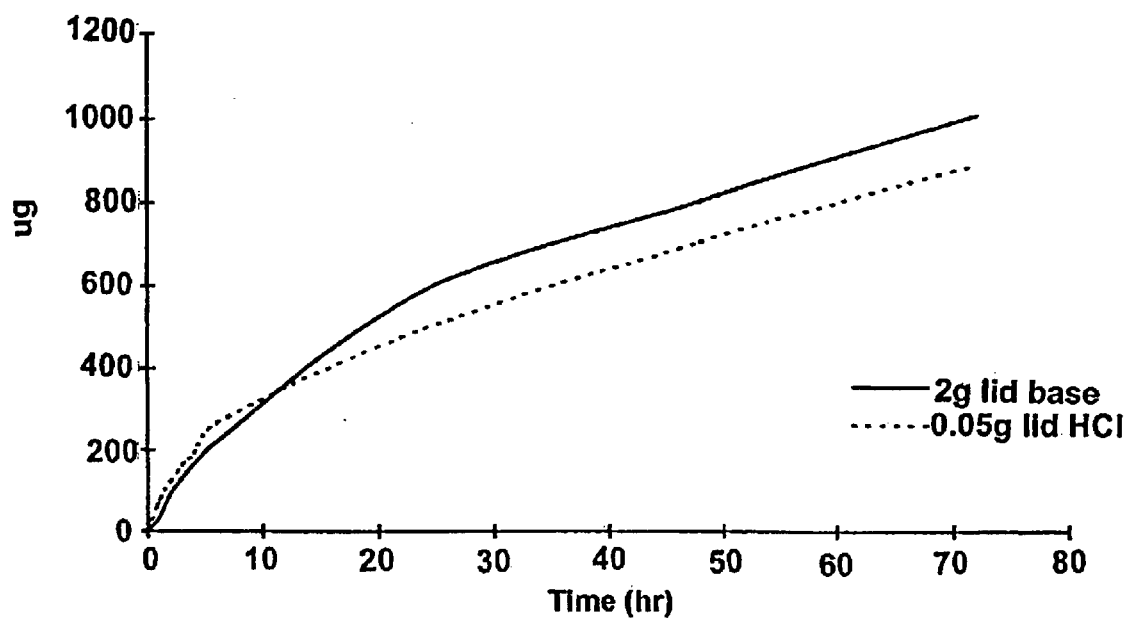
FIGS. 6A and 6B is a graph showing release profiles of crystalline lidocaine base and crystalline lidocaine HCl from DePuy CMW3 bone cement.
Figure 6B:
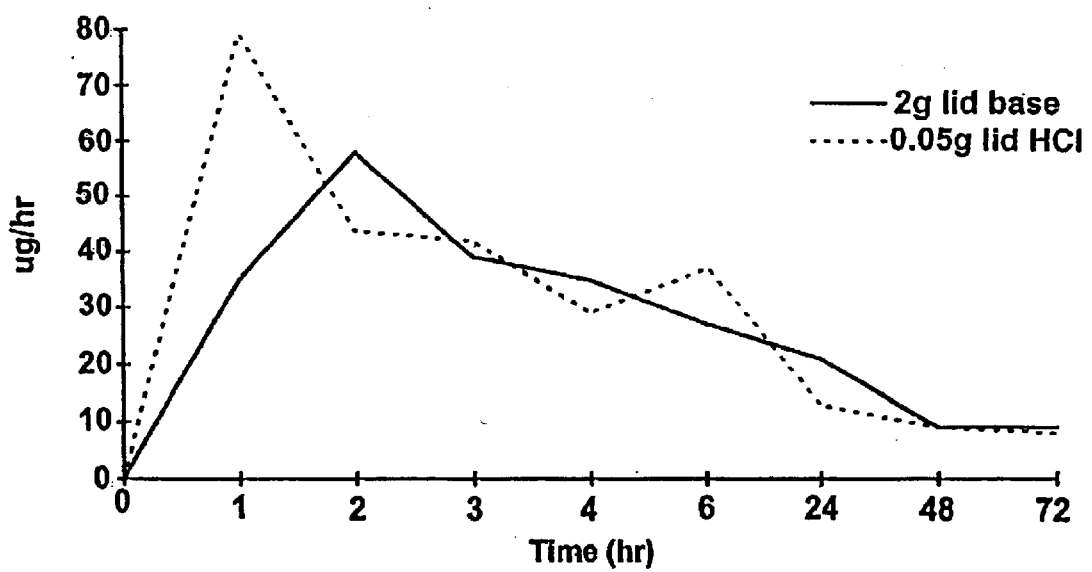

Thus, the studies of Example 2 clearly demonstrate that particular combinations of bone cement and anaesthetic may advantageously be chosen to achieve a desired result. The primary advantage of choosing a combination with superior release of anaesthetic is that less anaesthetic need be used. This is exemplified by the comparison below of 2.0 g lidocaine base with 0.05 g lidocaine HCl, from which it can be seen that 40 times less lidocaine HCl is required to achieve the same result as that achieved with lidocaine base (FIG. 6). Indeed, as shown in Example 2, efficacious amounts of crystalline lidocaine HCl are released from bone cement when 0.005 g of lidocaine are combined with 57.9 g wet bone cement (i.e., 0.0086% by weight of bone cement). The invention thus encompasses the use of potent, i.e., highly releasable, forms of anaesthetics in combination with bone cement. Further, the invention contemplates the use of compounds for increasing the potency or releasability of anaesthetics from bone cement.

A further advantage of choosing a particular combination as taught by the invention is that, in combinations where release of anaesthetic is greater initially, the desired efficacy (i.e. pain reduction or elimination) is achieved within a shorter period following application of the bone cement and anaesthetic combination. For example, elution of liquid prilocaine base from CMW3 bone cement is initially greater than that of its crystalline counterpart as well as either form of lidocaine base (see FIG. 4). On the other hand, where a slower initial release of anaesthetic is desired, use of crystalline prilocaine base, for example, in CMW3 bone cement would be suitable.

That the compositions, process, and method of the invention are efficacious in clinical applications can be seen from the results of a knee replacement surgery described in Example 3. From this example, it is apparent that lidocaine is eluted from Howmedica bone cement and within 6 hours of the application of the bone cement, sufficient lidocaine has eluted to provide an analgesic effect which persists for at least 24 hours and probably at least several days before the anaesthetic is metabolized in the body.

An additional study was undertaken to address the question of whether the incorporation of an anaesthetic into bone cement according to the invention produces any undesirable effects on the mechanical properties of bone cement (see Example 4). Lidocaine (Xylocaine, Astra Pharmaceuticals) was combined with DePuy CMW3 bone cement as described in Example 1, and mechanical properties including dough time, setting time, exotherm, compressive strength, flexural strength, flexural modulus, and impact strength were analyzed.

As can be seen from Table 1, the incorporation of lidocaine into bone cement had no negative effects on the mechanical properties of the bone cement. In fact, there was a small increase in impact strength and an increase in dough time and setting time, which increases may be considered advantageous under certain circumstances.

It will, of course, be appreciated that other proprietary bone cements can equally well be employed, such as, for example, Palacos®R which is distributed by Schering Plough in Europe and by Richards in North America. The invention also contemplates incorporation of local anaesthetics into proprietary bone wax compositions, such as Ethicon® Bone Wax, which is a sterile mixture of beeswax and isopropyl palmitate, a wax softening used to control bleeding from bone surfaces. The invention further contemplates incorporation of local anaesthetics into injectable bone substitutes, or bone paste, such as Norian Skeletal Repair System (Norican SRS™) developed by Norian Corporation of Cupertino, Calif., which is a calcium phosphate based cement which, when injected, forms carbonated apatite.

EXAMPLE 1

Method

Forty grams of bone cement powder from each of three manufacturers: Howmedica (Simplex), Zimmer (Osteobond) and DePuy (CMW3), were mixed with 0.5, 1.0 and 2.0 g of gas-sterilized crystalline lidocaine base (Xylocaine, Astra Pharmaceuticals). The polymerization initiated mixtures were formed into discs 50 mm×1 mm and allowed to harden. The hardened discs were then placed in a stirred solution (100 ml) containing 0.2% saline at 37° C. 100 µl aliquots were taken at 1, 2, 3, 4, 6, 24, 48 and 72 hours and subjected to HPLC with electrochemical detection analysis to determine the lidocaine level in each sample.

Results

Typical elution profiles are shown in FIGS. 1 (Howmedica), 2 (Zimmer) and 3 (DePuy). These profiles demonstrate that lidocaine elutes from the bone cement mixture in an amount proportional to the amount of lidocaine in the mixture. The rate of elution is at a maximum during the first 24 hours and then tapers off. The curves also indicate that there is a peak dose at about the 6 hour point. The peak dose then provides sustained release over a 72-hour test period. It also appears that elution occurs mainly from the surface of the disc and is related to the porosity and other surface properties of the disc.

EXAMPLE 2

Method

Crystalline lidocaine base from three manufacturers (Sigma, Spectrum, and Wyckoff) was used in these studies. It was observed that the relative proportions of crystals of different size varied substantially among the three brands. Thus, an initial study compared the effect of crystal size on elution and release characteristics using Spectrum lidocaine base. Crystals were sorted using a series of molecular sieves into three groups (small, 75 to 150 um; medium, 150 to 250 um; and large, >250 um) and 2.0 g samples from each group were incorporated into bone cement and tested, as indicated below.

All studies adhered to the following procedure: Forty grams of bone cement (DePuy CMW3 unless otherwise specified) were mixed with 2.0, 0.5, 0.05, or 0.005 g of liquid or crystalline anaesthetic (lidocaine: Sigma, Spectrum, Wyckoff; prilocaine: Colour Your Enzyme, Queen's University, Kingston, Ontario, Canada). The polymerization initiated mixtures were formed into discs 50 mm×1 mm and allowed to cure. The cured discs were then placed in a solution (100 ml) containing 0.2% saline, and kept at 37° C. in a shaking water bath. 1 ml aliquots were taken at 0, 1, 2, 3, 4, 6, 24, 48 and 72 hours and to each was added 1 µg/ml bupivacaine as an internal standard. 50 µl aliquots were subjected to HPLC using a Beckman reverse phase column having a mobile phase of 40 mM ammonium phosphate:acetonitrile (60:40) and a flow rate of 1 ml/min, followed by electrochemical detection, to determine the amount of anaesthetic in each sample.

The percentage of anaesthetic released was calculated from the mass of the bone cement/anaesthetic mixture: anaesthetic (e.g., 0.05 g)+bone cement powder (40 g)+bone cement liquid (17.9 g)=57.95 g. The mean mass of bone cement discs in an individual experiment was, for example, 3.75 g, which corresponds to 15.45 discs per mixture. For elution of, for example, 1000 ug after 72 hours, 1000 ug×15.45 discs=0.015 g anaesthetic released. Since 0.05 g anaesthetic was used, 30.9% was released.

Studies examined the effects of manufacturer of anaesthetic, type of anaesthetic (i.e., lidocaine vs. prilocaine), physical form (i.e., crystalline vs. liquid), particle size, type of bone cement, concentration of anaesthetic, and chemical form (i.e., base vs. HCl) on release profiles (i.e., the amount of anaesthetic released after a given period and the change in rate of elution of anaesthetic over time).

Results

Manufacturer of Lidocaine Base

Crystalline lidocaine base produced by the three manufacturers had similar elution profiles. In each case, about 1% of the 2.0 g of lidocaine was released over 72 hours.

Prilocaine Base vs. Lidocaine Base

Figure 4A:
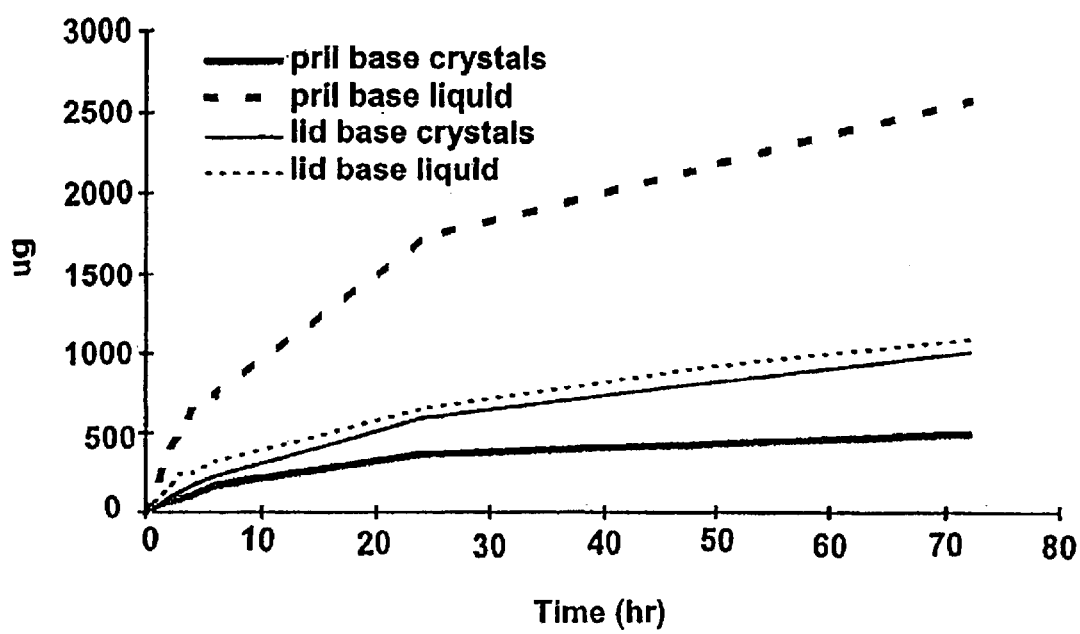
FIGS. 4A and 4B is a graph showing release profiles of crystalline and liquid lidocaine and prilocaine base from DePuy CMW3 bone cement.
Figure 4B:
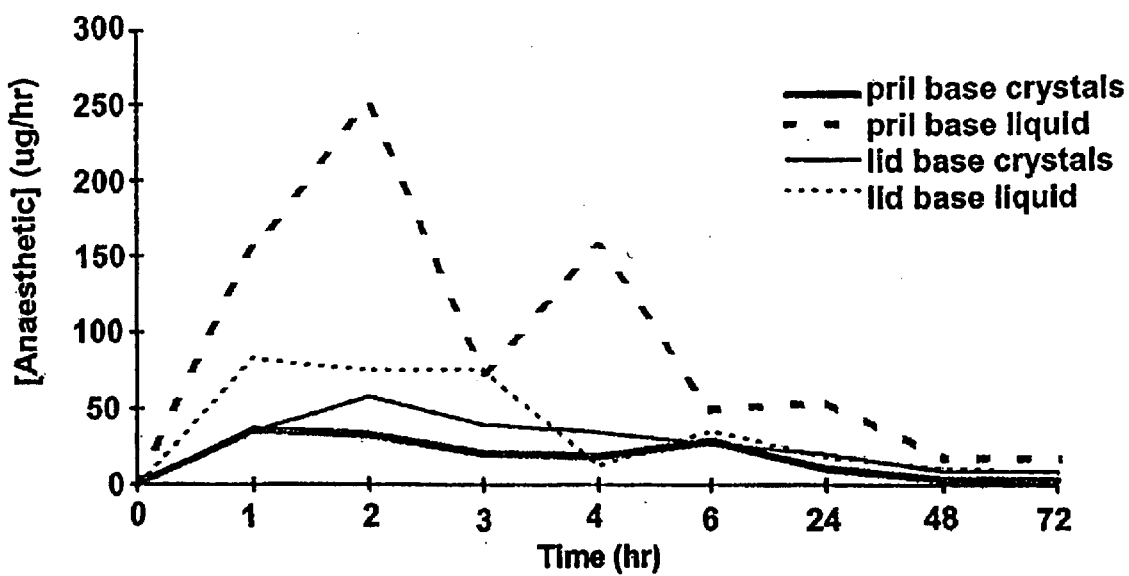

As shown in FIG. 4, elution and release of crystalline forms of both anaesthetics were the same, with about 0.4% and 1% of the 2.0 g of each of prilocaine and lidocaine, respectively, being released. Initial release of anaesthetic was greatest for liquid prilocaine base. Further, about 2% of liquid prilocaine base was released, while only 1% of liquid lidocaine base was released.

Crystalline vs. Liquid Anaesthetic

Lidocaine Base: Elution characteristics of crystalline and liquid lidocaine base were the same. In both cases, about 1% of the 2 g of lidocaine was released over 72 hours.

Lidocaine HCl: As shown in FIG. 5, about 25% of the 0.05 g of crystalline lidocaine HCl was released from CMW3 bone cement. In contrast, only 0.3% of the 0.05 g sample of liquid lidocaine HCl was released.

Prilocaine Base: There was a difference between crystalline and liquid prilocaine, wherein 0.4% of the 2.0 g of crystals, and 2% of the 2.0 g of liquid was released.

Particle Size

Lidocaine Base: There was no effect of particle size on the release profile or overall release of lidocaine base. In all size groups (75 to 150 um, 150 to 250 um, and >250 um), about 1% of the 2.0 g of lidocaine used was released over the 72 hour period.

Lidocaine HCl: Smaller particles eluted faster, such that elution during the latter portion of the 72 hour period was predominantly from larger particles. Overall, 30 to 34% of the lidocaine of the 0.05 g samples was released for all three ranges of particle size. Similar results were obtained with 0.005 g samples, with 17 to 26% overall release.

DePuy CMW3 Bone Cement vs. DePuy CMW Endurance Bone Cement

Lidocaine Base: Release of crystalline lidocaine base from CMW3 bone cement was about 1% after 72 h in CMW3, and only about 0.3% after 72 h in CMW Endurance.

Lidocaine HCl: A similar effect of type of bone cement was obtained when 0.5 g samples of crystalline lidocaine HCl were used, wherein about 33% was released from CMW3, and 23% from CMW Endurance.

Prilocaine Base: Release of crystalline prilocaine base from both types of bone cement was similar, and about 0.4% of the 2.0 g of prilocaine was released. However, substantially more liquid prilocaine base was released from CMW3 than from CMW Endurance (2% vs about 0.3%).

Concentration of Crystalline Lidocaine HCl

There was no apparent substantive difference in elution profile of three concentrations of lidocaine HCl (0.5, 0.05, and 0.005 g per 40 g bone cement). At 0.5 g, release was about 33%; at 0.05 g, about 25%; and at 0.005 g, 17 to 26%.

Lidocaine Base vs. Lidocaine HCl

Comparison of 2.0 g lidocaine base with 0.05 g lidocaine HCl indicated that the two forms of lidocaine had similar release profiles (see FIG. 6). However, because of the differences in release, approximately 40 times less anaesthetic is needed to achieve the same effect if lidocaine HCl is used, rather than lidocaine base.

EXAMPLE 3

A female patient, 68 years old, having a previous total knee replacement and a below-the-knee amputation, presented with latent infection in the knee. A revision to remove the knee prosthesis was performed and the cut ends of the bone were treated with an anti-bacterial bone cement to keep the bones spaced. Three weeks later, the bone cement was removed and tissue samples were taken for laboratory analysis for signs of infection. Bone cement was temporarily applied to keep the bones spaced and aligned, but this time the cement was Howmedica bone cement containing 2 g of lidocaine (Xylocaine) per 40 g package of cement. The lidocaine-containing bone cement was gas sterilized but not irradiated. After recovery from anaesthesia the patient reported severe pain in the knee for a period of approximately 6 hours and thereafter no pain at all. 24 hours post surgery, the patient was sleeping without the aid of pain killers and was also able to receive physiotherapy without feeling undue discomfort.

EXAMPLE 4

The effects of lidocaine (Xylocaine) on the mechanical properties of Depuy CMW3 bone cement were evaluated and are summarized in Table 1 below.

TABLE 1

| Cement Property | CMW3 | CMW3 + Lidocaine |
|---|---|---|
| Dough time (min:sec) | 2:50 | 7:05 |
| Setting time (min:sec) | 10:06 | 14:20 |
| Exotherm (° C.) | 70.8 | 69.1 |
| Compressive strength (Mpa) | 112.0 | 113.3 |
| Flexural strength (Mpa) | 65.0 | 66.3 |
| Flexural modulus (Mpa) | 2785 | 2753 |
| Impact strength (J/m) | 3.03 | 3.61 |

From Table 1 it can be seen that addition of lidocaine to CMW3 improves impact strength by about 10%, but has little effect on compressive strength, flexural strength or flexural modulus. It is particularly noted that lidocaine additions increase the cement setting time by about 40% and the "doughing time," i.e., the time needed to reach a working mix that can be readily handled, by a factor of 3.

Those skilled in the art will recognize, or be able to ascertain through routine experimentation, equivalents to the specific embodiments described herein. Such equivalents are considered to be within the scope of this invention and are covered by the appended claims.

What is claimed is:

1. An anaesthetic bone cement composition, comprising:
   (a) a bone cement comprising:
      (i) a liquid monomeric (meth)acrylate composition; and
      (ii) a powder comprising at least one of a homopolymer and a copolymer of methyl methacrylate containing an effective amount of a polymerization initiator; and
   (b) an analgesic effective amount up to about 5% by weight of a local anaesthetic agent, wherein at least a portion of the anaesthetic agent is released from said bone cement composition when the bone cement composition is in a subject and the strength of the bone cement is substantially unchanged.

2. The anaesthetic bone cement composition of claim 1, wherein said local anaesthetic agent is selected from the group consisting of lidocaine, bupivacaine, prilocaine, and tetracaine.

3. The anaesthetic bone cement composition of claim 1, further comprising a radiopacifier.

4. The anaesthetic bone cement composition of claim 1, wherein said local anaesthetic agent is a liquid.

5. The anaesthetic bone cement composition of claim 1, wherein said local anaesthetic agent is a solid.

6. The anaesthetic bone cement composition of claim 1, wherein said local anaesthetic is an acid.

7. The anaesthetic bone cement composition of claim 1, wherein said local anaesthetic agent is a base.

8. The anaesthetic bone cement composition of claim 1, wherein said local anaesthetic agent is released from the bone cement in a preselected characteristic release profile that is determined by at least one of chemical form and physical form of the anaesthetic.

9. The anaesthetic bone cement composition of claim 1, wherein said local anaesthetic agent is present in an amount between about 0.007% and about 5% by weight of said anaesthetic bone cement composition.

10. The anaesthetic bone cement composition of claim 1, wherein said local anaesthetic agent is provided in at least two different forms selected from the group consisting of acid, base, solid, and liquid.

11. The anaesthetic bone cement composition of claim 1, wherein said local anaesthetic agent comprises a combination of at least two anaesthetic agents selected from the group consisting of lidocaine, bupivacaine, prilocaine, and tetracaine.

12. The anaesthetic bone cement composition of claim 11, wherein said at least two local anaesthetic agents are provided in at least two different forms, the forms being selected from the group consisting of acid, base, solid, and liquid.

13. The anaesthetic bone cement composition of claim 11, wherein said at least two local anaesthetic agents are provided in the same form, the form being selected from the group consisting of acid, base, solid, and liquid.

14. The anaesthetic bone cement composition of claim 11, wherein said polymerization initiator is an organic peroxy compound.

15. The anaesthetic bone cement composition of claim 14, wherein said organic peroxy compound is benzoyl peroxide.

* * * * *

UNITED STATES PATENT AND TRADEMARK OFFICE
CERTIFICATE OF CORRECTION

PATENT NO. : 6,713,527 B2
DATED : March 30, 2004
INVENTOR(S) : David M. Bond et al.

It is certified that error appears in the above-identified patent and that said Letters Patent is hereby corrected as shown below:

Column 12,
Line 24, "claim 11" should be -- claim 1 --

Signed and Sealed this

First Day of February, 2005

JON W. DUDAS
*Director of the United States Patent and Trademark Office*